US009759650B2

(12) United States Patent
Katsuyama et al.

(10) Patent No.: US 9,759,650 B2
(45) Date of Patent: Sep. 12, 2017

(54) FILLING-CAPACITY MEASURING METHOD

(71) Applicant: JAPAN TOBACCO INC., Tokyo (JP)

(72) Inventors: Norio Katsuyama, Tokyo (JP); Hiroshi Yuasa, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 126 days.

(21) Appl. No.: 13/908,698

(22) Filed: Jun. 3, 2013

(65) Prior Publication Data

US 2013/0268239 A1 Oct. 10, 2013

Related U.S. Application Data

(63) Continuation of application No. PCT/JP2012/057168, filed on Mar. 21, 2012.

(30) Foreign Application Priority Data

Mar. 22, 2011 (WO) .................. PCT/JP2011/056802

(51) Int. Cl.
| | |
|---|---|
| *G06F 17/18* | (2006.01) |
| *G01N 21/25* | (2006.01) |
| *G01N 21/359* | (2014.01) |
| *G01N 21/3563* | (2014.01) |

(52) U.S. Cl.
CPC ........... *G01N 21/25* (2013.01); *G01N 21/359* (2013.01); *G01N 21/3563* (2013.01)

(58) Field of Classification Search
CPC ... G01N 21/25; G01N 21/3563; G01N 21/359
USPC .................................................. 702/179, 189
See application file for complete search history.

(56) References Cited

U.S. PATENT DOCUMENTS

| | | | | |
|---|---|---|---|---|
| 4,186,756 A | * | 2/1980 | Takemoto | .............. A24B 15/16 |
| | | | | 131/355 |
| 4,733,080 A | | 3/1988 | Brunnschweiler et al. | |
| 4,805,641 A | | 2/1989 | Radzio et al. | |
| 4,819,668 A | * | 4/1989 | Shelar et al. | ................. 131/371 |

(Continued)

FOREIGN PATENT DOCUMENTS

| | | |
|---|---|---|
| CN | 1665407 A | 9/2005 |
| EP | 0843974 A2 | 5/1998 |

(Continued)

OTHER PUBLICATIONS

Explorable.com (Jun. 18, 2009). Multiple Regression Analysis. Retrieved Feb. 26, 2015 from Explorable.com:https://explorable.com/multiple-regression-analysis.*

(Continued)

*Primary Examiner* — Stephanie Bloss
(74) *Attorney, Agent, or Firm* — Birch, Stewart, Kolasch & Birch, LLP

(57) ABSTRACT

In order to provide a method for measuring a filling capacity of a raw material such as leaf tobacco without carrying out a complicated operation, the present invention includes the steps of (i) irradiating a near infrared ray on a sample of a raw material so as to measure a transmission absorption spectrum or a diffuse reflectance spectrum of the sample; and (ii) calculating an estimated filling capacity value by use of the transmission absorption spectrum or the diffuse reflectance spectrum thus measured and on the basis of a calibration curve which has been prepared in advance.

3 Claims, 6 Drawing Sheets

(56) References Cited

U.S. PATENT DOCUMENTS

| | | | |
|---|---|---|---|
| 4,865,054 | A | 9/1989 | Lorenzen et al. |
| 4,941,482 | A | 7/1990 | Heitmann et al. |
| 4,986,285 | A | 1/1991 | Radzio et al. |
| 5,010,904 | A | 4/1991 | Lassiter |
| 5,251,648 | A | 10/1993 | Ogawa et al. |
| 5,469,872 | A * | 11/1995 | Beard et al. .................. 131/291 |
| 5,873,982 | A | 2/1999 | Yoshimura et al. |
| 6,281,498 | B1 | 8/2001 | Fellows |
| 6,763,838 | B2 | 7/2004 | Suzuki et al. |
| 2002/0030820 | A1 | 3/2002 | Kida et al. |
| 2002/0107644 | A1 | 8/2002 | Meglen et al. |
| 2003/0102001 | A1 | 6/2003 | Suzuki |
| 2005/0011528 | A1* | 1/2005 | Rae .............................. 131/280 |
| 2006/0090767 | A1 | 5/2006 | Fleischhauer et al. |

FOREIGN PATENT DOCUMENTS

| | | | |
|---|---|---|---|
| EP | 1 236 990 | A1 | 9/2002 |
| EP | 1 302 117 | A1 | 4/2003 |
| JP | 52-034783 | | 3/1977 |
| JP | 61-213649 | A | 9/1986 |
| JP | 62-032868 | A | 2/1987 |
| JP | 63-200049 | A | 8/1988 |
| JP | 4-144675 | A | 5/1992 |
| JP | 5-273125 | A | 10/1993 |
| JP | 06-197746 | A | 7/1994 |
| JP | 6-288892 | A | 10/1994 |
| JP | 7-310223 | A | 11/1995 |
| JP | 9-292338 | A | 11/1997 |
| JP | 2000-074828 | A | 3/2000 |
| JP | 2000-333663 | A | 12/2000 |
| JP | 2001-017084 | A | 1/2001 |
| JP | 2002-153251 | A | 5/2002 |
| JP | 2002-340792 | A | 11/2002 |
| JP | 2009-275314 | A | 11/2009 |
| JP | 2011-017565 | A | 1/2011 |
| RU | 2250452 | C2 | 4/2005 |
| WO | WO 02/03818 | A1 | 1/2002 |
| WO | WO 02/35211 | A1 | 5/2002 |
| WO | WO 2007/075027 | A1 | 7/2007 |

OTHER PUBLICATIONS

Zhang et al., "Quantitative analysis of routine chemical consituents in tobacco by near-infrared spectroscopy and support vector machine", Apr. 2008, pp. 1408, 1413.*

"Analysis Method of Leaf Tobacco," Japan Tobacco and Salt Public Corporation, Jan. 1976, 1984 edition, pp. 56-60.

Duan et al., "FT-NIR Spectroscopic Determination of Five Key Chemical Components in Tobacco Sheets," Laser & Infrared, Oct. 2007, vol. 37, No. 10, pp. 1058-1061.

English Abstract of Jarvis et al., "Macromolecular biophysics of the plant cell wall: Concepts and methodology," Plant Physiol Biochem, 2000, vol. 38, pp. 1-13.

English Abstract of Jin-Song et al., "Analysis of Ash, Total Volatile Acids and Total Volatile Bases in Tobacco with Near Infrared Spectroscopy," Journal of Instrument analysis, May 2007, pp. 655-657, 661.

English Abstract of Wang et al., "Establishment of rapid determination model of petroleum ether extract on tobacco by using near infrared reflectance spectroscopy," Guangdong Agricultural Science, Feb. 2007.

English Abstract of X et al., "Application of PCA-SVR to NIR prediction model for tobacco chemical composition," Guang pu xue yu guang pu fen xi, 2007, vol. 27, pp. 2460-2463.

Hana et al., "Applying artificial neural networks. I. Estimating nicotine in tobacco from near infrared data," Journal of Near Infrared Spectroscopy, 1995, vol. 3, pp. 133-142.

Ma et al.,"Determination of Chemical Component in Tobacco Leaves by FT-NIR Spectroscopy: Study of Influence of Spectral Ranges on PLS Modeling," Spectroscopy and Spectral Analysis, Apr. 2004, vol. 24, No. 4, pp. 444-446.

Soutome et al., "Development of non-destructive estimation model for strawberry fruit hardness," Proceedings of presentation, Joint Conference on Environmental Engineering in Agriculture, 2006, pp. 1428.

Verrier et al., "Contribution of near infra-red spectrometry (NIRS) to detect nicotine conversion to nornicotine in Burley tobacco," CORESTA Meeting, 2009.

Office Action issued in corresponding Russian Patent Appliction No. 2013131286 dated Jun. 26, 2014.

Ma Aiguo, et al., "Study on Appearance Characters and Internal Quality of Different Stalk Position Flue Cured Tobacco Leaves," Shandong Agricultural Sciences, 1994-2014 China Academic Journal, Electronic Publishing House (pp. 48-51) Dec. 31, 2009 (http://www.cnki.net).

Maria Isabella Sifola, "Quality Characteristics of Burley Tobacco Irrigated with Saline Water," Field Crops Researcy, Dec. 31, 2005.

Russian Notice of Allowance dated Oct. 23, 2014 for Russian Application No. 2013131286/28 with English translation.

Office Action issued in corresponding Japanese Application No. 2014-121812 dated Mar. 3, 2015 (with English translation).

* cited by examiner

FILLING-CAPACITY MEASURING METHOD

CROSS-REFERENCE TO RELATED APPLICATIONS

This application is a Continuation of PCT International Application No. PCT/JP2012/057168 filed in Japan on Mar. 21, 2012, which claims the benefit of PCT International Application No. PCT/JP2011/056802 filed in Japan on Mar. 22, 2011, the entire contents of which are hereby incorporated by reference.

TECHNICAL FIELD

The present invention relates to a method for measuring a filling capacity of cut tobacco, specifically a method for measuring a filling capacity of cut tobacco by use of near infrared spectroscopy.

BACKGROUND ART

In production design of a cigarette, it is necessary to consider various chemical properties and physical properties of leaf tobacco. A filling capacity of cut tobacco is one of the physical properties of the leaf tobacco. The filling capacity is a numerical value of a volume of 1 g of leaf tobacco which has been compressed at a certain pressure for a certain time period after being cut into the form of cut rags. That is, in a case where the filling capacity of cut tobacco is high, it is possible to produce a large number of cigarettes per weight of the cut tobacco. Further, measurement of the filling capacity makes it possible to estimate the number of cigarettes which can be manufactured from 1 kg of cut leaf tobacco. As such, the filling capacity of the cut tobacco is useful for production planning and also allows, in variety development and blending design, selecting and using leaf tobacco which requires a low production cost. Accordingly, the filling capacity of the cut tobacco is (i) an important factor in terms of cost for a raw material as well as (ii) an essential element for the production design.

Near infrared spectroscopy, in which factors such as a transmission absorption spectrum or a diffuse reflectance spectrum of a sample are measured by irradiating a near infrared ray on the sample, allows non-destructive and prompt measurement of the factors and is therefore widely used in various fields.

CITATION LIST

Patent Literature

[Patent Literature 1]
Japanese Patent Application Publication, Tokukai, No. 2001-17084 A (Publication Date: Jan. 23, 2001)
[Patent Literature 2]
Japanese Patent Application Publication, Tokukai, No. 2000-74828 A (Publication Date: Mar. 14, 2000)
Non-Patent Literature
[Non-Patent Literature 1]
Hidehira SOUTOME et al., "Development of non-destructive estimation model of strawberry fruit firmness (Ichigo Kajitsu Kodo no Hihakai Suitei Model no Kaihatsu)," Proceedings of Presentation Joint Conference on Environmental Engineering in Agriculture (CD-ROM), 2006, p. 1428.

[Non-Patent Literature 2]
VERRIER J. L. et al, Contribution of near infrared spectroscopy (NIRS) to detect nicotine conversion to nornicotine in Burley tobacco, CORESTA Meeting, 2009.
[Non-Patent Literature 3]
HANA M. et al, J. of Near Infrared Spectrosc., 1995, 3, 133-142.
[Non-Patent Literature 4]
MA X. et al, Determination of chemical components in tobacco leaves by FT-NIR spectroscopy: study of influence of spectral ranges on PLS modeling, Chinese Journal of Spectroscopy Laboratory 2003-02.
[Non-Patent Literature 5]
DUAN Y.-q. et al, FT-NIR Spectroscopic Determination of Five Key Chemical Components in Tobacco Sheets, Laser & Infrared 2007-10.

SUMMARY OF INVENTION

Technical Problem

According to a conventional filling capacity measuring method, a filling capacity of leaf tobacco in a form of cut rags is measured by means of a measuring device after the cut leaf tobacco is conditioned, in a conditioning chamber which is strictly regulated to a certain temperature and a certain humidity, for 2 to 7 days until the cut leaf tobacco reaches an equilibrium state. In general, in order to obtain an accurate measured value, the filling capacity of the cut leaf tobacco is repeatedly measured two to five times, and an average of values of the filling capacity thus measured is calculated. That is, the conventional filling capacity measuring method requires an extremely large amount of time and effort.

Meanwhile, a conventional technique which uses the near infrared spectroscopy in measuring a property of leaf tobacco is used for measuring a chemical substance (e.g., ash content, total volatile acid or base, nicotine, total sugar, total nitrogen, potassium, chlorine, reducing sugar, and organic matter) in cut tobacco or a leaf. There is known no example in which the near infrared spectroscopy is used for measuring a physical property of the leaf tobacco. Further, it is also unknown whether or not the near infrared spectroscopy can be used for measuring the physical property of the leaf tobacco.

Thus, the present invention is accomplished in view of the problem described above. An object of the present invention is to provide a method for measuring a filling capacity of cut tobacco without carrying out a complicated operation.

Solution to Problem

As a result of diligent study in view of the above-mentioned problem, the inventors found that it was possible to measure a filling capacity of cut tobacco by use of near infrared spectroscopy. Based on the finding, the inventors accomplished the present invention.

In order to attain the object, a filling capacity measuring method in accordance with the present invention is a method for measuring a filling capacity of leaf tobacco, including the steps of: (i) irradiating a near infrared ray on a sample of a raw material so as to measure a transmission absorption spectrum or a diffuse reflectance spectrum of the sample; and (ii) calculating an estimated filling capacity value by use of the transmission absorption spectrum or the diffuse reflectance spectrum thus measured and on the basis of a calibration curve which has been prepared in advance.

Moreover, the present invention further encompasses a filling capacity measuring method which is a method for measuring a filling capacity of a raw material, including the steps of: (i) irradiating a near infrared ray on a sample of a raw material, a filling capacity of which is considered important, so as to measure a transmission absorption spectrum or a diffuse reflectance spectrum of the sample; and (ii) calculating an estimated filling capacity value by use of the transmission absorption spectrum or the diffuse reflectance spectrum thus measured and on the basis of a calibration curve which has been prepared in advance.

Advantageous Effects of Invention

According to the filling capacity measuring method in accordance with the present invention, it is possible to promptly measure, without carrying out a complicated operation, a filling capacity of a raw material such as leaf tobacco whose filling capacity is considered important.

DESCRIPTION OF EMBODIMENTS

Figure 1:
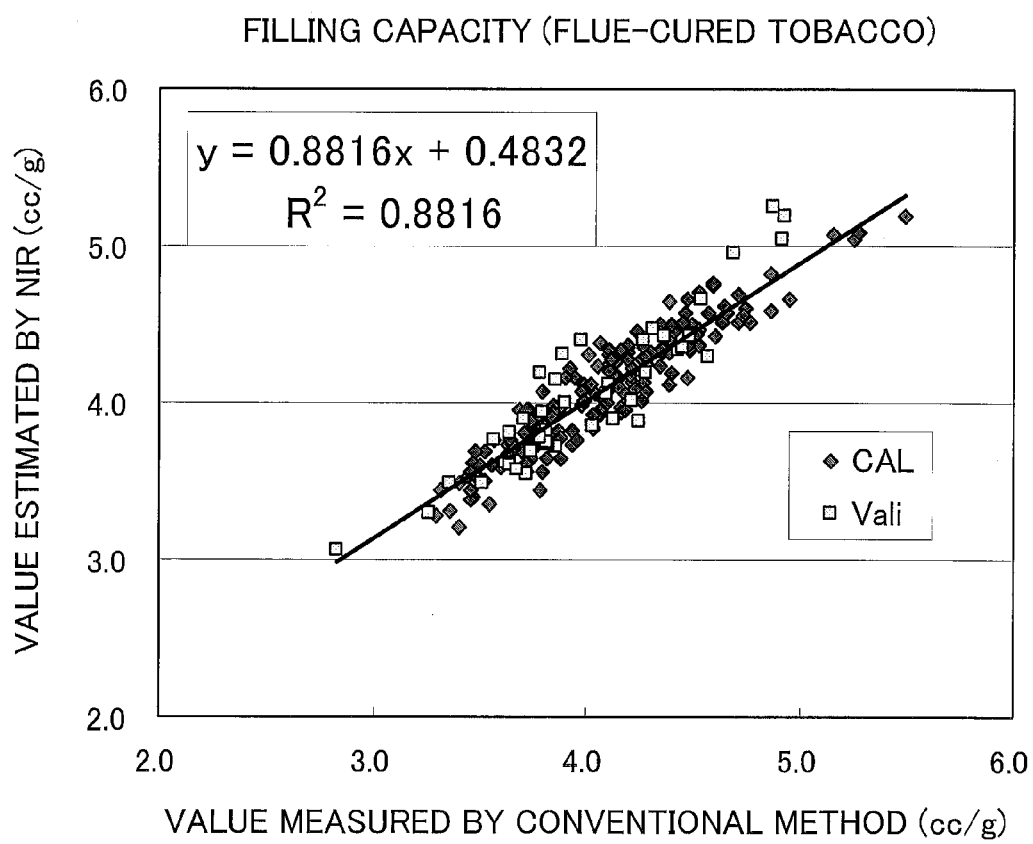
FIG. 1 is a view showing a correlation between (i) a filling capacity value measured by near infrared spectroscopy by using a calibration curve which has been prepared by carrying out multiple regression analysis and (ii) a filling capacity value measured by a conventional filling capacity measuring method.

One embodiment of a filling capacity measuring method in accordance with the present invention is described below.

The filling capacity measuring method in accordance with the present invention is a method for measuring a filling capacity of a raw material, including the steps of: (i) irradiating a near infrared ray on a sample of a raw material, a filling capacity of which is considered important, so as to measure a transmission absorption spectrum or a diffuse reflectance spectrum of the sample; and (ii) calculating an estimated filling capacity value by use of the transmission absorption spectrum or the diffuse reflectance spectrum thus measured and on the basis of a calibration curve which has been prepared in advance.

Hereinafter, a transmission absorption spectrum and a diffuse reflectance spectrum which are obtained by irradiating a near infrared ray are referred to as "near-infrared spectrum."

A raw material which can be used as a sample to which the measuring method of the present invention is applied is a raw material whose filling capacity is considered important. Examples of such a raw material encompass cotton, linen, wool, herbal medicine, and tobacco.

A form of a raw material which can be used as a sample to which the measuring method of the present invention is applied is not particularly limited. Examples of the form encompass cut rags and powder. In a case where the raw material is leaf tobacco, the form can be cut rags, powder, a lamina (strip part), a sheet piece, or the like, preferably cut rags or powder, and more preferably powder.

In one embodiment, the filling capacity measuring method in accordance with the present invention is a method for measuring a filling capacity of leaf tobacco, including the steps of: (i) irradiating a near infrared ray on a sample of a raw material so as to measure a transmission absorption spectrum or a diffuse reflectance spectrum of the sample; and (ii) calculating an estimated filling capacity value by use of the transmission absorption spectrum or the diffuse reflectance spectrum thus measured and on the basis of a calibration curve which has been prepared in advance. As an example, a case where a filling capacity of the leaf tobacco is measured is described below.

The filling capacity of the leaf tobacco is constituted by a volume of cut rags and a space between the cut rags. The volume of the cut rags is a factor determined by an amount of the cut rags and can be estimated on the basis of an apparent density. The space between the cut rags is a factor determined on the basis of a property of the cut rags and is affected by elastic modulus, a shape of the cut rags, and an orientation (arrangement) of the cut rags. Accordingly, the filling capacity cannot be estimated only on the basis of the apparent density.

The filling capacity is a physical property amount expressed in a unit of "cc/g", and is a numerical value of a volume of 1 g of leaf tobacco in a form of cut rags which was compressed at a certain pressure for a certain time period after being cut into the form of cut rags. According to a conventional filling capacity measuring method, the filling capacity is a value of a volume of 1 g of leaf tobacco in a form of cut rags which is obtained, in order to fill a cigarette roll with the leaf tobacco, in such a manner that (i) leaf tobacco is cut into the form of cut rags each having a width of approximately 0.8 mm and a length of 1 mm to 10 mm, (ii) the leaf tobacco thus cut is conditioned in a conditioning chamber, which is strictly regulated to a certain temperature (22° C.) and a certain humidity (60% RH), for 2 to 7 days until the leaf tobacco reaches an equilibrium state (equilibrium moisture content: 10% to 12%), and (iii) then a certain weight (g) of the leaf tobacco thus cut is compressed at a certain pressure for a certain time period.

Leaf tobacco and a type of leaf tobacco to be used for the measurement of the present invention are not limited. It is possible to measure any leaf tobacco and any type of leaf tobacco which are conventionally used for a cigarette.

Examples of such leaf tobacco and type of tobacco encompass cut tobacco, sheet tobacco, and expanded cut tobacco (cut tobacco subjected to an expansion processing) of flue-cured tobacco, burley tobacco, oriental tobacco, or domestic tobacco.

Moisture adjustment of a sample to be used for the measurement is not particularly required, and it is possible to measure the sample as long as the sample has a moisture content of 6% to 13%. For this reason, the measuring method of the present invention does not require strict moisture adjustment, which is required for a conventional filling capacity measuring method described below.

Moreover, an amount of the sample required for the measurement is much less than that required for the conventional filling capacity measuring method described below. For example, in a case where the sample is in a form of powder, approximately 1 g to 2 g per sample is sufficient for the measurement. Even in a case where the sample is in a form of cut rags, less than 10 g per sample is sufficient for the measurement.

According to the measuring method in accordance with the present invention, a sample of the leaf tobacco should be in the identical form with that of a sample of the leaf tobacco used in preparing a calibration curve. In order to increase uniformity of the sample, it is preferable to use a sample in a form of powder (powdered tobacco) which is produced by powdering leaf tobacco by means of a grinder. By increasing the uniformity of the sample, it is possible to increase accuracy of the measurement. In general, in content component analysis of the leaf tobacco, the measurement is carried out by use of the powdered tobacco. As such, in a case where the powdered tobacco is used as a measurement sample, a sample for the content component analysis can be used as it is in measurement of a filling capacity. Further, a sample used in the measurement of a filling capacity can be used as it is in another content component analysis.

In measurement of a filling capacity of a sample whose filling capacity is unknown, a near infrared ray to be irradiated on the sample of leaf tobacco may be in a wavelength region of 800 nm to 2500 nm, in which wavelength region at least a given wavelength used for calculating a filling capacity on the basis of a calibration curve is included. For measurement of near-infrared spectrum, it is possible to use a near infrared spectroscopic measurement device (NIR), which is generally used for the near infrared spectroscopy.

A wavelength, in the near-infrared spectrum which is measured, to be actually used in the measurement of a filling capacity varies depending on leaf tobacco and a type of leaf tobacco, or a calibration curve. A wavelength to be used in the measurement of a filling capacity can be determined by a method (described later) for preparing a calibration curve. For example, in a case where the filling capacity is measured by use of an estimated equation A5 in Example 1 (described below), near infrared rays having a wavelength of at least approximately 1342.5 nm, 1736.5 nm, 1830.5 nm, 2345.0 nm, and 2432.5 nm should be irradiated. In a case where the calibration curve is obtained by using PLS (Partial Least Squares) regression analysis, all wavelengths used in the PLS regression analysis are used in the measurement of a filling capacity by the near infrared spectroscopy.

In a case where a method for measuring another item by use of the near infrared spectroscopy (e.g., a method for measuring nicotine by use of the near infrared spectroscopy, a method for measuring a chemical substance in leaf tobacco by the near infrared spectroscopy, etc.) is known, it is possible to measure the another item and the filling capacity simultaneously by including a wavelength that is used in the measurement of the another item.

It is preferable that a calibration curve used for calculating a filling capacity in the measuring method of the present invention be prepared by multivariate analysis by use of near-infrared spectra of a plurality of samples of leaf tobacco whose filling capacity is known. As such, in a case where the calibration curve does not exist, it is preferable that the measuring method of the present invention further include a step of preparing the calibration curve by multivariate analysis after measuring the near-infrared spectra of the plurality of samples of leaf tobacco whose filling capacity is known.

As multivariate analysis, it is possible to use multiple regression analysis (MLR: Multiple Linear Regression), the PLS (Partial Least Squares) regression analysis, principal component regression analysis, and Fourier transform analysis. In particular, the multiple regression analysis and the PLS regression analysis are preferable.

The number of the plurality of samples of leaf tobacco to be used for preparing the calibration, the filling capacity of which leaf tobacco is known, is preferably not less than 30 samples, and more preferably 70 samples or more. The larger the number of samples is, the more accurate the calibration curve becomes. For this reason, there is no upper limit for the number of samples. For example, the upper limit can be set to not more than 2000, or to a number more than 2000.

As used herein, "leaf tobacco whose filling capacity is known" indicates leaf tobacco whose filling capacity has been measured by the conventional filling capacity measuring method. According to the conventional filling capacity measuring method, (i) leaf tobacco is cut into a form of cut rags, (ii) the leaf tobacco thus cut is conditioned in a conditioning chamber, which is strictly regulated to 22±1.0° C. and 60±3.0% RH, for 2 to 7 days until the leaf tobacco reaches an equilibrium state, and (iii) then the filling capacity of the leaf tobacco is measured in the conditioning chamber by means of a filling capacity measuring device. A small-sized filling capacity measuring device requires 10 g to 15 g cut tobacco per measurement, whereas a large-sized filling capacity measuring device requires 60 g to 100 g of cut tobacco per measurement. In general, in order to obtain an accurate measured value, a filling capacity of cut tobacco is repeatedly measured two to five times, and an average of values of the filling capacity thus measured is calculated. Moreover, measurement by means of the filling capacity measuring device requires approximately 20 minutes per sample.

A wavelength region of the near-infrared spectrum for preparing a calibration curve may be appropriately selected and can be 800 nm to 2500 nm, for example. However, the wavelength region is not limited to this, and a narrower wavelength region is acceptable. Further, it is possible to measure the near-infrared spectrum by carrying out the scanning with near infrared rays at any regular wavelength intervals (e.g., every 0.5 nm) within the wavelength region.

Next, a specific method for preparing a calibration curve is described below.

First, a sample of cut tobacco whose filling capacity is known is irradiated with near infrared rays at regular intervals (e.g., 0.5-nm intervals) within a certain wavelength region (e.g., 800 nm to 2500 nm), each of which near infrared rays is monochromatic light obtained by spectral diffraction. Since the near infrared rays are transmitted through and absorbed by the sample and/or reflected from the sample so as to be diffused, an intensity of monochromatic light which is not absorbed by the sample is measured by means of a detector. A spectrum of an absorption intensity of each wavelength in the sample is displayed on the basis of a difference from a reference intensity measured in advance, and information on the spectrum thus displayed is obtained as data. This processing is carried out with respect to a plurality of samples, preferably not less than 30 samples, so that a plurality of data of spectrum information are obtained. After a transmission absorption spectrum or a diffuse reflectance spectrum of each of the data is measured, the transmission absorption spectrum or the diffuse reflectance spectrum is converted to a second-derivative spectrum. Principal component analysis is carried out by use of the second-derivative spectrum thus obtained and a filling capacity value measured by use of the conventional filling capacity measuring method, and a principal component (dominant wavelength) which contributes to an objective variable (filling capacity value) is selected. Then, the multivariate analysis such as the multiple regression analysis and the PLS regression analysis is carried out, so that a calibration curve is prepared.

Once the calibration curve is prepared, the calibration curve can be used from the next measurement, so that the step of preparing a calibration curve becomes unnecessary.

In a case where transmission absorption spectra or diffuse reflectance spectra are measured by use of a plurality of varieties of leaf tobacco such as flue-cured tobacco, burley tobacco, oriental tobacco, and domestic tobacco, so as to prepare one calibration curve by using the transmission absorption spectra and the diffuse reflectance spectra, it is possible to measure filling capacities of samples of different varieties of leaf tobacco by use of the common calibration curve.

As described above, according to the filling capacity measuring method of the present invention, time and equipment required for the conditioning becomes unnecessary. As such, it is not necessary to carry out complicated preparation and complex measurement which demands considerable skills. This makes it possible to measure a filling capacity more easily and promptly than the conventional filling capacity measuring method. Further, compared with the conventional filling capacity measuring method, the measurement can be completed in shorter time (approximately 1/20) and requires a smaller amount of sample. Moreover, a result obtained by the measurement has a high correlation with that obtained by the conventional filling capacity measuring method. In particular, in a case where powdered tobacco is used as a measurement sample, the measurement can be carried out with high accuracy by use of 1 g to 2 g of the sample per unit sample.

The following description discusses more details of embodiments of the present invention by showing examples. It goes without saying that the present invention is not limited to the examples described below but allows details in various states. Further, the present invention is not limited to the above-described embodiments but allows various modifications within the scope of the claims. Thus, any embodiment derived from an appropriate combination of two or more technical means disclosed will also be included in the technical scope of the present invention. Moreover, all documents mentioned herein are incorporated as a reference.

EXAMPLES

Example 1

Filling Capacity Measurement of Flue-Cured Tobacco (Preparation of Calibration Curve)

Cut tobacco of flue-cured tobacco inside or outside of Japan, a filling capacity of which had been measured by the conventional filling capacity method, was powdered by means of a grinder. The leaf tobacco thus powdered and passed through a sieve of the grinder, which sieve had a mesh of approximately 1 mm, was used as a sample for calibration curve preparation. A measurement of a transmission absorption spectrum of the sample for calibration curve preparation was carried out at 0.5-nm intervals in a near infrared wavelength region of 800 nm to 2500 nm. Specifically, approximately 1 g to 2 g of the sample for calibration curve preparation was packed in a quartz vial (diameter: 29 mm) and suppressed by use of a special tool.

Then, by means of a near infrared spectroscopic measurement device (manufactured by FOSS NIRSystems, Inc., model: XM-1100), a transmission absorption spectrum was measured by (i) irradiating near infrared rays from a bottom of the vial so as to detect, with respect to each wavelength, a near infrared ray which was reflected and (ii) comparing the near infrared ray thus detected and a reference intensity.

After transmission absorption spectra of respective 176 samples for calibration curve preparation were measured, a calibration curve was prepared by analyzing, by use of a multivariate analysis method, a correlation between the transmission absorption spectra and the filling capacity obtained by the conventional filling capacity measuring method. Specifically, by means of general-purpose VISION software (manufactured by FOSS NIRSystems, Inc.) which was built in the near infrared spectroscopic measurement device, (i) the transmission absorption spectra of the samples were spectrum-converted by a second differentiation, and (ii) principal component analysis was carried out by use of (a) a known filling capacity value as an objective variable and (b) a dominant wavelength as a principal component. Then, a calibration curve was prepared by the multiple regression analysis. As a result, the following estimated equations (A1) through (A5) were obtained. Ys obtained by the estimated equations are estimated filling capacity values. K(1) through K(5) indicate absorbances of wavelengths of 1342.5 nm, 1736.5 nm, 2345.0 nm, 2432.5 nm, and 1830.5 nm, respectively, which absorbances were subjected to a differential processing after the transmission absorption spectra were measured.

In the estimated equations, coefficients of determination ($R^2$) were 0.720 to 0.882, and standard errors were 0.144 to 0.219.

TABLE 1

| Estimated equation | Coefficient of determination | Standard error |
|---|---|---|
| (A1): Y = −1023.1K(1) + 8.4847 | 0.720 | 0.219 |
| (A2): Y = −1023.1K(1) + 164.21K(2) + 8.4847 | 0.812 | 0.180 |
| (A3): Y = −1023.1K(1) + 164.21K(2) − 194.63K(3) + 8.4847 | 0.834 | 0.170 |
| (A4): Y = −1023.1K(1) + 164.21K(2) − 194.63K(3) − 171.6K(4) + 8.4847 | 0.870 | 0.151 |
| (A5): Y = −1023.1K(1) + 164.21K(2) − 194.63K(3) − 171.6K(4) + 211.56K(5) + 8.4847 | 0.882 | 0.144 |

FIG. 1 shows, with respect to each of the samples for calibration curve preparation, a correlation between the filling capacity value obtained by the conventional filling capacity measuring method and the estimated filling capacity value obtained by the near infrared spectroscopy by using the estimated equation (A5) (see "CAL" in FIG. 1).

(Filling Capacity Measurement by Near Infrared Spectroscopy)

A spectrum measurement was carried out by near infrared spectroscopy with respect to cut flue-cured tobacco, whose filling capacity value was unknown. Then, a filling capacity of the cut flue-cured tobacco was estimated by using the calibration curve. First, in the same manner as preparation of the sample for calibration curve preparation, the cut flue-cured tobacco, whose filling capacity value was unknown, was powdered by means of the grinder and put through a sieve so as to serve as a measurement sample. Then, with respect to each of 43 measurement samples obtained in this manner, a transmission absorption spectrum was measured and an estimated filling capacity value was calculated by use of (i) absorbances of wavelengths of 1342.5 nm, 1736.5 nm, 1830.5 nm, 2345.0 nm, and 2432.5 nm, which absorbances were subjected to a differential processing after the spectrum measurement was performed and (ii) the estimated equation (A5). Note that measurement of one sample required not more than one minute.

After a filling capacity of each of the measurement samples was estimated by the near infrared spectroscopy, the filling capacity of the each of the measurement samples was measured by the conventional filling capacity measuring method. Then, a correlation between the estimated filling capacity value obtained by the near infrared spectroscopy and the filling capacity value obtained by the conventional filling capacity measuring method was examined. The result is shown in FIG. 1 (see "Vali" in FIG. 1).

As shown in FIG. 1, the filling capacity value obtained by the conventional filling capacity measuring method and the estimated filling capacity value obtained by the near infrared spectroscopy had a high correlation with each other. That is, the method of the present invention for measuring a filling capacity by the near infrared spectroscopy makes it possible to accurately and conveniently measure a filling capacity of cut tobacco.

Example 2

Filling Capacity Measurement of Burley Tobacco (Preparation of Calibration Curve)

A calibration curve was prepared by the multiple regression analysis in the same manner as Example 1, except that 177 samples of burley tobacco inside or outside of Japan were used as a sample for calibration curve preparation. As a result, the following estimated equations (B1) through (B5) were obtained. Ys obtained by the estimated equations below are estimated filling capacity values. K(1) through K(5) indicate absorbances of wavelengths of 1152.5 nm, 2263.5 nm, 2360.0 nm, 1792.5 nm, and 1892.5 nm, respectively, which absorbances were subjected to a differential processing after the transmission absorption spectra were measured.

In the estimated equations, coefficients of determination ($R^2$) were 0.55589 to 0.7556, and standard errors were 0.1636 to 0.2173.

TABLE 2

| Estimated equation | Coefficient of determination | Standard error |
| --- | --- | --- |
| (B1): Y = −1240.02K(1) + 6.1372 | 0.5589 | 0.2173 |
| (B2): Y = −1240.02K(1) + 37.63K(2) + 6.1372 | 0.6424 | 0.1962 |
| (B3): Y = −1240.02K(1) + 37.63K(2) − 398.83K(3) + 6.1372 | 0.7022 | 0.1796 |
| (B4): Y = −1240.02K(1) + 37.63K(2) − 398.83K(3) − 552.63K(4) + 6.1372 | 0.7397 | 0.1684 |
| (B5): Y = −1240.02K(1) + 37.63K(2) − 398.83K(3) − 552.63K(4) − 58.4K(5) + 6.1372 | 0.7556 | 0.1636 |

Figure 2:
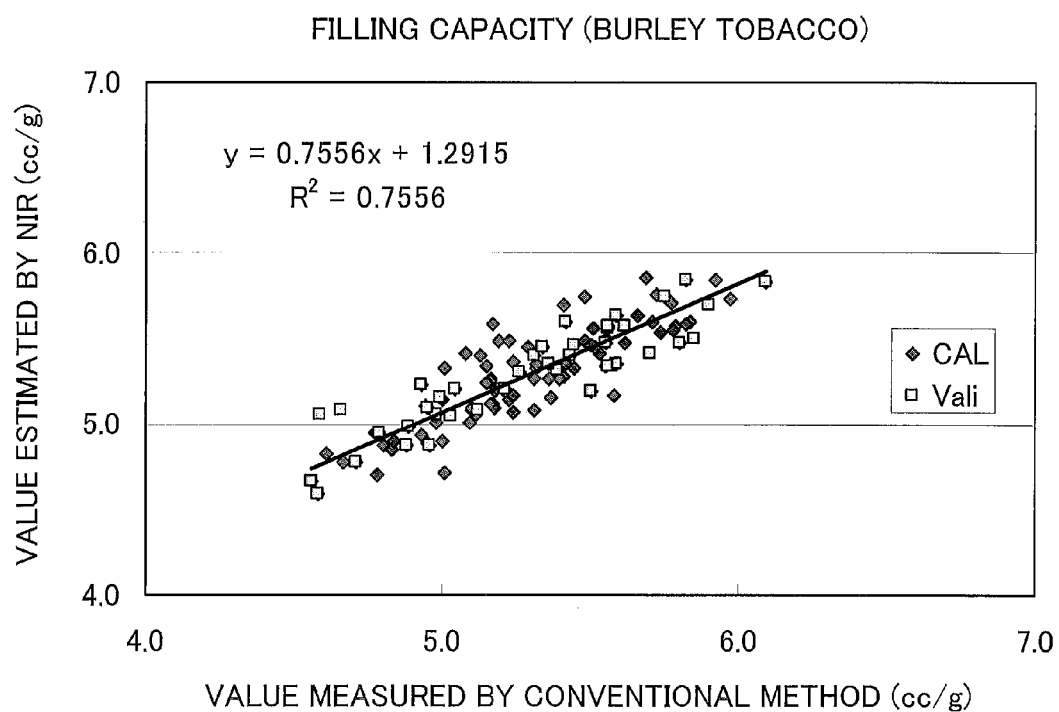
FIG. 2 is a view showing a correlation between (i) a filling capacity value measured by the near infrared spectroscopy by using a calibration curve which has been prepared by carrying out the multiple regression analysis and (ii) a filling capacity value measured by the conventional filling capacity measuring method.

FIG. 2 shows, with respect to each of the samples for calibration curve preparation, a correlation between the filling capacity value obtained by the conventional filling capacity measuring method and the estimated filling capacity value obtained by the near infrared spectroscopy by using the estimated equation (B5) (see "CAL" in FIG. 2).

(Filling Capacity Measurement by Near Infrared Spectroscopy)

A spectrum measurement was carried out by near infrared spectroscopy with respect to cut burley tobacco, whose filling capacity value was unknown. Then, a filling capacity of the cut burley tobacco was estimated by using the calibration curve. First, in the same manner as preparation of the sample for calibration curve preparation, the cut burley tobacco, whose filling capacity value was unknown, was powdered by means of the grinder and put through a sieve so as to serve as a measurement sample. Then, with respect to each of 47 measurement samples obtained in this manner, a transmission absorption spectrum was measured and an estimated filling capacity value was calculated by use of (i) absorbances of wavelengths of 1152.5 nm, 1792.5 nm, 1892.5 nm, 2263.5 nm, and 2360.0 nm, which absorbances were subjected to a differential processing after the spectrum measurement was performed and (ii) the estimated equation (B5).

After a filling capacity of each of the measurement samples was estimated by the near infrared spectroscopy, the filling capacity of the each of the measurement samples was measured by the conventional filling capacity measuring method. Then, a correlation between the estimated filling capacity value obtained by the near infrared spectroscopy and the filling capacity value obtained by the conventional filling capacity measuring method was examined. The result is shown in FIG. 2 (see "Vali" in FIG. 2).

As shown in FIG. 2, also in a case where leaf tobacco which was of different variety from that used in Example 1, the filling capacity value obtained by the conventional filling capacity measuring method and the estimated filling capacity value obtained by the near infrared spectroscopy had a high correlation with each other.

Example 3

Filling Capacity Measurement of Oriental Tobacco (Preparation of Calibration Curve)

A calibration curve was prepared by the multiple regression analysis in the same manner as Example 1, except that 71 samples of oriental tobacco inside or outside of Japan were used as a sample for calibration curve preparation. As a result, the following estimated equations (C1) through (C5) were obtained. Ys obtained by the estimated equations below are estimated filling capacity values. K(1) through K(5) indicate absorbances of wavelengths of 2264.0 nm, 2357.0 nm, 1515.5 nm, 1701.0 nm, and 1207.0 nm, respectively, which absorbances were subjected to a differential processing after the transmission absorption spectra were measured.

In the estimated equations, coefficients of determination ($R^2$) were 0.5534 to 0.7828, and standard errors were 0.1749 to 0.2435.

TABLE 3

| Estimated equation | Coefficient of determination | Standard error |
|---|---|---|
| (C1): Y = 194.7694K(1) + 3.4479 | 0.5534 | 0.2435 |
| (C2): Y = 194.7694K(1) − 368.7977K(2) + 3.4479 | 0.6243 | 0.225 |
| (C3): Y = 194.7694K(1) − 368.7977K(2) + 445.7412K(3) + 3.4479 | 0.703 | 0.2015 |
| (C4): Y = 194.7694K(1) − 368.7977K(2) + 445.7412K(3) + 224.1757K(4) + 3.4479 | 0.7677 | 0.1796 |
| (C5): Y = 194.7694K(1) − 368.7977K(2) + 445.7412K(3) + 224.1757K(4) − 154.84334K(5) + 3.4479 | 0.7828 | 0.1749 |

Figure 3:
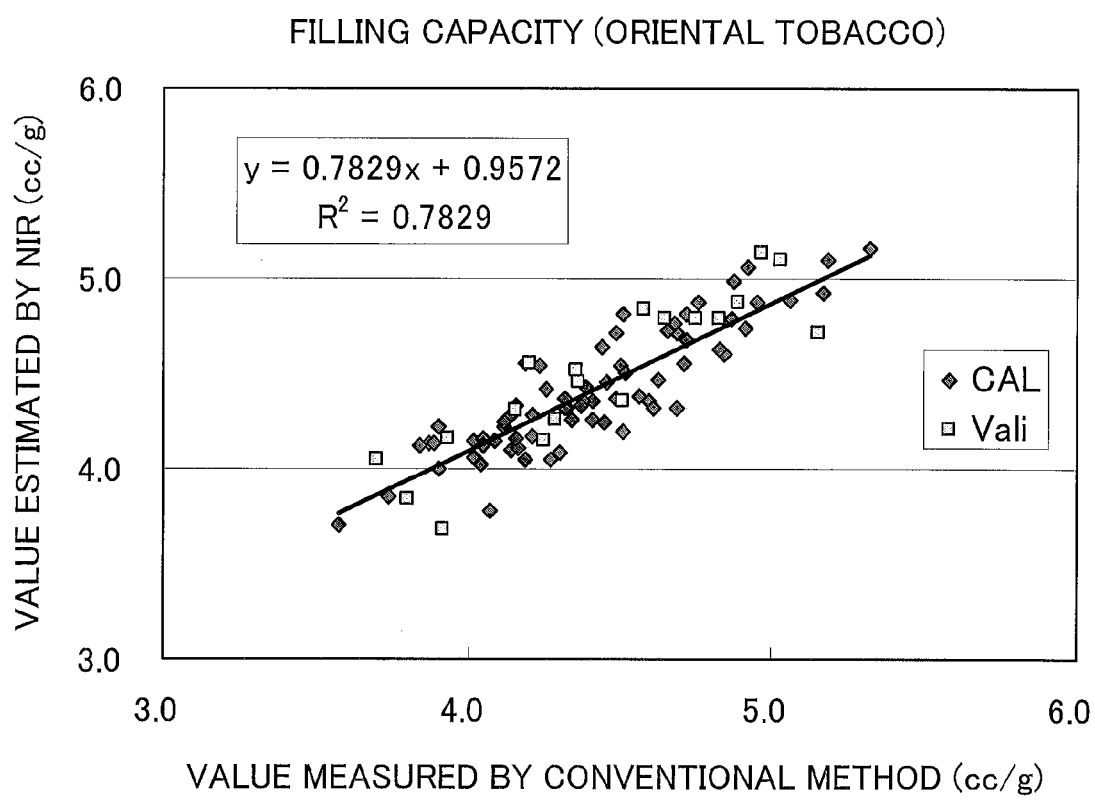
FIG. 3 is a view showing a correlation between (i) a filling capacity value measured by the near infrared spectroscopy by using a calibration curve which has been prepared by carrying out the multiple regression analysis and (ii) a filling capacity value measured by the conventional filling capacity measuring method.

FIG. 3 shows, with respect to each of the samples for calibration curve preparation, a correlation between the filling capacity value obtained by the conventional filling capacity measuring method and the estimated filling capacity value obtained by the near infrared spectroscopy by using the estimated equation (C5) (see "CAL" in FIG. 3).

(Filling Capacity Measurement by Near Infrared Spectroscopy)

A spectrum measurement was carried out by near infrared spectroscopy with respect to cut oriental tobacco, whose filling capacity value was unknown. Then, a filling capacity of the cut oriental tobacco was estimated by using the calibration curve. First, in the same manner as preparation of the sample for calibration curve preparation, the cut oriental tobacco, whose filling capacity value was unknown, was powdered by means of the grinder and put through a sieve so as to serve as a measurement sample. Then, with respect to each of 19 measurement samples obtained in this manner, a transmission absorption spectrum was measured and an estimated filling capacity value was calculated by use of (i) absorbances of wavelengths of 1207.0 nm, 1515.5 nm, 1701.0 nm, 2264.0 nm, and 2357.0 nm, which absorbances were subjected to a differential processing after the spectrum measurement was performed and (ii) the estimated equation (C5).

After a filling capacity of each of the measurement samples was estimated by the near infrared spectroscopy, the filling capacity of the each of the measurement samples was measured by the conventional filling capacity measuring method. Then, a correlation between the estimated filling capacity value obtained by the near infrared spectroscopy and the filling capacity value obtained by the conventional filling capacity measuring method was examined. The result is shown in FIG. 3 (see "Vali" in FIG. 3).

As shown in FIG. 3, also in a case where leaf tobacco which was of different variety from that used in Examples 1 and 2, the filling capacity value obtained by the conventional filling capacity measuring method and the estimated filling capacity value obtained by the near infrared spectroscopy had a high correlation with each other.

Example 4

Filling Capacity Measurement of Flue-Cured Tobacco, Burley Tobacco and Oriental Tobacco (Preparation of Calibration Curve)

A calibration curve was prepared by the multiple regression analysis in the same manner as Example 1, except that a total of 424 samples for calibration curve preparation were used, which samples were made up of 176 samples of flue-cured tobacco, 177 samples of burley tobacco, and 71 samples of oriental tobacco. As a result, the following estimated equations (D1) through (D5) were obtained. Ys obtained by the estimated equations below are estimated filling capacity values. K(1) through K(5) indicate absorbances of wavelengths of 1341.0 nm, 2439.0 nm, 2355.0 nm, 2077.5 nm, and 1977.0 nm, respectively, which absorbances were subjected to a differential processing after the transmission absorption spectra were measured.

In the estimated equations, coefficients of determination ($R^2$) were 0.7731 to 0.8961, and standard errors were 0.2204 to 0.3237.

TABLE 4

| Estimated equation | Coefficient of determination | Standard error |
|---|---|---|
| (D1): Y = −697.8573K(1) + 6.3222 | 0.7731 | 0.3237 |
| (D2): Y = −697.8573K(1) − 296.6902K(2) + 6.3222 | 0.8272 | 0.2829 |
| (D3): Y = −697.8573K(1) − 296.6902K(2) − 275.4945K(3) + 6.3222 | 0.8597 | 0.2554 |
| (D4): Y = −697.8573K(1) − 296.6902K(2) − 275.4945K(3) − 128.1203K(4) + 6.3222 | 0.8806 | 0.2359 |
| (D5): Y = −697.8573K(1) − 296.6902K(2) − 275.4945K(3) − 128.1203K(4) − 96.0222K(5) + 6.3222 | 0.8961 | 0.2204 |

Figure 4:
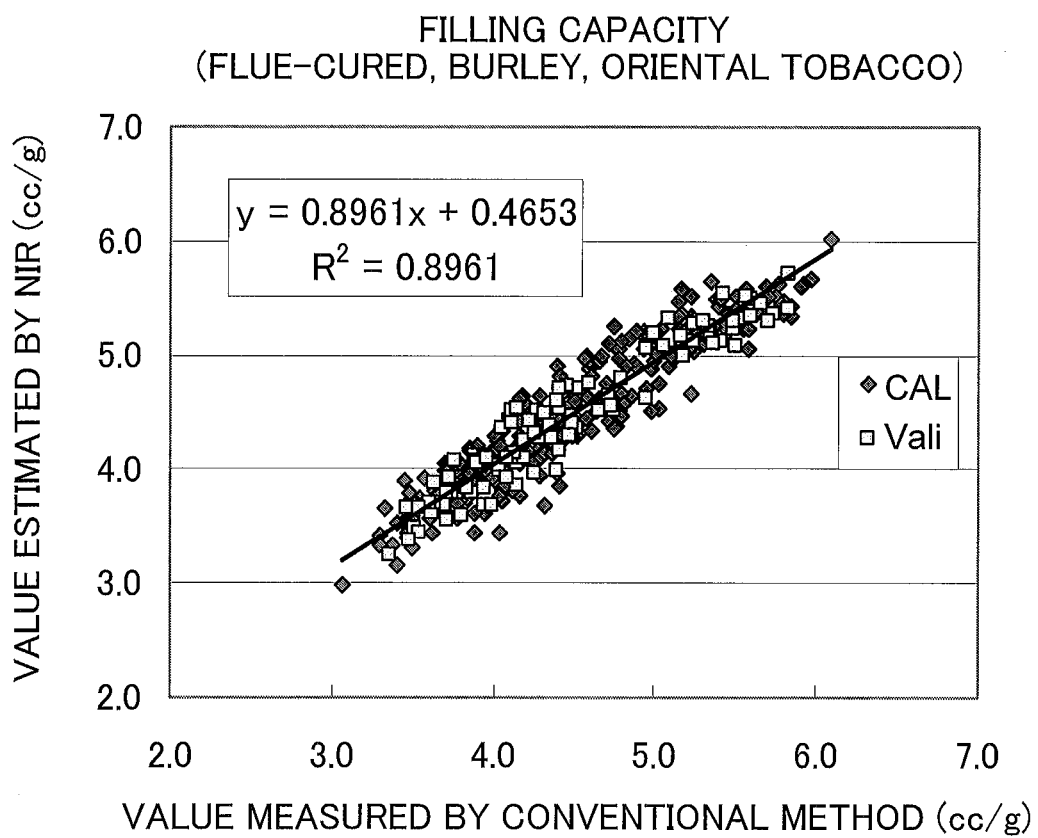
FIG. 4 is a view showing a correlation between (i) a filling capacity value measured by the near infrared spectroscopy by using a calibration curve which has been prepared by carrying out the multiple regression analysis and (ii) a filling capacity value measured by the conventional filling capacity measuring method.

FIG. 4 shows, with respect to each of the samples for calibration curve preparation, a correlation between the filling capacity value obtained by the conventional filling capacity measuring method and the estimated filling capacity value obtained by the near infrared spectroscopy by using the estimated equation (D5) (see "CAL" in FIG. 4).

(Filling Capacity Measurement by Near Infrared Spectroscopy)

A spectrum measurement was carried out by near infrared spectroscopy with respect to cut flue-cured tobacco, cut burley tobacco, and cut oriental tobacco, a filling capacity value of each of which was unknown. Then, a filling capacity of each of the cut flue-cured tobacco, the cut burley tobacco, and the cut oriental tobacco was estimated by using the calibration curve. First, in the same manner as preparation of the samples for calibration curve preparation, the cut flue-cured tobacco, the cut burley tobacco, and the cut oriental tobacco, a filling capacity value of each of which was unknown, were powdered by means of the grinder and put through a sieve so as to serve as measurement samples. Then, with respect to each of the measurement samples made up of 43 samples of the flue-cured tobacco, 47 samples of the burley tobacco, and 19 samples of the oriental tobacco, a transmission absorption spectrum was measured and an estimated filling capacity value was calculated by use of (i) absorbances of wavelengths of 1341.0 nm, 1977.0 nm, 2077.5 nm, 2355.0 nm, and 2439.0 nm, which absorbances were subjected to a differential processing after the spectrum measurement and (ii) the estimated equation (D5).

After a filling capacity of each of the measurement samples was estimated by the near infrared spectroscopy, the filling capacity of the each of the measurement samples was measured by the conventional filling capacity measuring method. Then, a correlation between the estimated filling capacity value obtained by the near infrared spectroscopy and the filling capacity value obtained by the conventional filling capacity measuring method was examined. The result is shown in FIG. 4 (see "Vali" in FIG. 4).

As shown in FIG. 4, also in a case where a calibration curve was prepared by use of a plurality of different varieties of leaf tobacco, the filling capacity value obtained by the conventional filling capacity measuring method and the estimated filling capacity value obtained by the near infrared spectroscopy had a high correlation with each other. That is, even in a case where different varieties of leaf tobacco are used as measurement samples, it is possible to accurately measure a filling capacity of cut tobacco by using a common calibration curve.

Example 5

Filling Capacity Measurement of Flue-Cured Tobacco, Burley Tobacco, Oriental Tobacco, and Domestic Tobacco by PLS Regression Analysis (Preparation of Calibration Curve)

By use of a total of 1421 samples for calibration curve preparation, which samples were made up of 640 samples of flue-cured tobacco inside or outside of Japan, 568 samples of burley tobacco inside or outside of Japan, 142 samples of oriental tobacco inside or outside of Japan, and 71 samples of domestic tobacco inside or outside of Japan, a transmission absorption spectrum of each of the samples for calibration curve preparation was measured in the same manner as Example 1. A correlation between the transmission absorption spectrum thus measured and the filling capacity measured by the conventional filling capacity method was analyzed by using the PLS regression analysis. Specifically, by use of the general-purpose VISION software (manufactured by FOSS NIRSystems, Inc.) which was built in the near infrared spectroscopic measurement device, the transmission absorption spectra of the samples were spectrum-converted by a second differentiation, and principal component analysis was carried out. Then, a calibration curve was prepared by using the PLS regression analysis. As a result, a calibration curve having a coefficient of determination ($R^2$) of 0.8977 and therefore having a correlation sufficient from a practical point of view was obtained.

Figure 5:
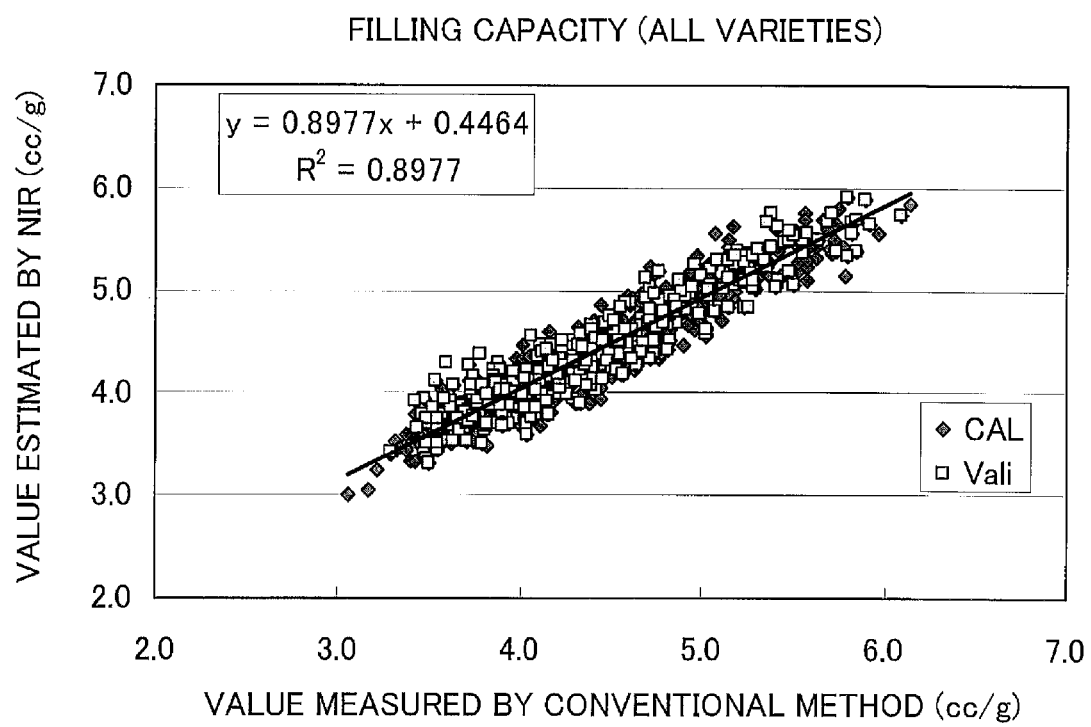
FIG. 5 is a view showing a correlation between (i) a filling capacity value measured by the near infrared spectroscopy by using a calibration curve which has been prepared by carrying out PLS regression analysis and (ii) a filling capacity value measured by the conventional filling capacity measuring method.

FIG. 5 shows, with respect to each of the samples for calibration curve preparation, a correlation between the filling capacity value obtained by the conventional filling capacity measuring method and the estimated filling capacity value obtained by the near infrared spectroscopy by using the estimated equation (see "CAL" in FIG. 5).

(Filling Capacity Measurement by Near Infrared Spectroscopy)

A spectrum measurement was carried out by near infrared spectroscopy with respect to cut flue-cured tobacco, cut burley tobacco, cut oriental tobacco, and cut domestic tobacco, a filling capacity value of each of which was unknown. Then, a filling capacity of each of the cut flue-cured tobacco, the cut burley tobacco, the cut oriental tobacco, and the cut domestic tobacco was estimated by using the calibration curve. First, in the same manner as preparation of the samples for calibration curve preparation, the cut flue-cured tobacco, the cut burley tobacco, the cut oriental tobacco, and the cut domestic tobacco, a filling capacity value of each of which was unknown, were powdered by means of the grinder and put through a sieve so as to serve as measurement samples. Then, with respect to each of 473 measurement samples obtained in this manner and made up of 213 samples of the flue-cured tobacco, 189 samples of the burley tobacco, 47 samples of the oriental tobacco, and 24 samples of the domestic tobacco, an absorption spectrum was measured at 0.5-nm intervals in a wavelength region of 800 nm to 2500 nm and an estimated filling capacity value was calculated by use of the estimated equation obtained above.

After a filling capacity of each of the measurement samples was estimated by the near infrared spectroscopy, the filling capacity of the each of the measurement samples was measured by the conventional filling capacity measuring method. Then, a correlation between the estimated filling capacity value obtained by the near infrared spectroscopy and the filling capacity value obtained by the conventional filling capacity measuring method was examined. The result is shown in FIG. 5 (see "Vali" in FIG. 5).

As shown in FIG. 5, also in a case where the PLS regression analysis was carried out as multivariate analysis, the filling capacity value obtained by the conventional filling capacity measuring method and the estimated filling capacity value obtained by the near infrared spectroscopy had a high correlation with each other. Further, it was demonstrated that also in a case where a calibration curve was prepared by the PLS regression analysis, it was possible to accurately measure filling capacities of different varieties of leaf tobacco by using a common calibration curve.

Example 6

Filling Capacity Measurement of Flue-Cured Tobacco, Burley Tobacco, Oriental Tobacco, and Domestic Tobacco by the PLS Regression Analysis by Use of Cut Samples (Preparation of Calibration Curve)

By use of a total of 631 samples for calibration curve preparation, which samples were made up of 284 samples of flue-cured tobacco inside or outside of Japan, 221 samples of burley tobacco inside or outside of Japan, 63 samples of oriental tobacco inside or outside of Japan, and 63 samples of domestic tobacco inside or outside of Japan, a transmission absorption spectrum of each of the samples for calibration curve preparation was measured in the same manner as Example 1. Note that cut tobacco itself was used in the measurement instead of samples in a form of powder. A correlation between the transmission absorption spectrum thus measured and the filling capacity measured by the conventional filling capacity method was analyzed by using the PLS regression analysis by the same method as used in Example 5. As a result, a calibration curve having a coefficient of determination ($R^2$) of 0.8811 and therefore having a correlation sufficient from a practical point of view was obtained.

Figure 6:
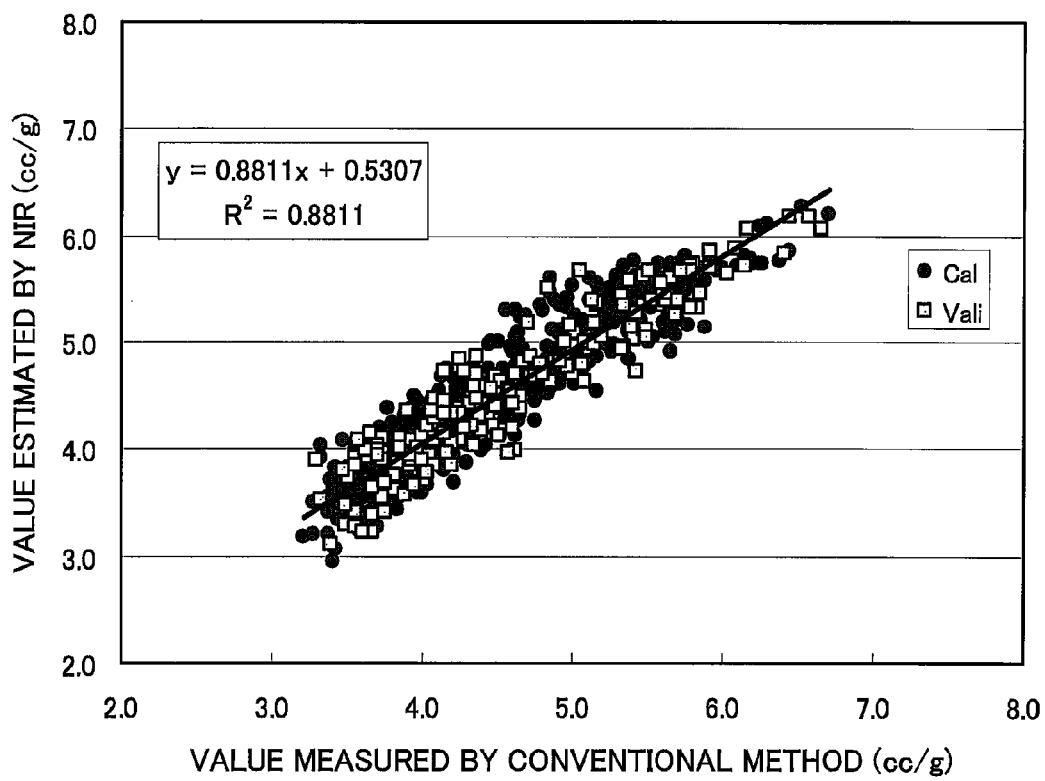
FIG. 6 is a view showing a correlation between (i) a filling capacity value measured by the near infrared spectroscopy by using a calibration curve which has been prepared by carrying out the PLS regression analysis by using a sample of cut tobacco and (ii) a filling capacity value measured by the conventional filling capacity measuring method.

FIG. 6 shows, with respect to each of the samples for calibration curve preparation, a correlation between the filling capacity value obtained by the conventional filling capacity measuring method and the estimated filling capacity value obtained by the near infrared spectroscopy by using the estimated equation (see "CAL" in FIG. 6).

(Filling Capacity Measurement by Near Infrared Spectroscopy)

A spectrum measurement was carried out by near infrared spectroscopy with respect to cut flue-cured tobacco, cut burley tobacco, cut oriental tobacco, and cut domestic tobacco, a filling capacity value of each of which was unknown. Then, a filling capacity of each of the cut flue-cured tobacco, the cut burley tobacco, the cut oriental tobacco, and the cut domestic tobacco was estimated by using the calibration curve. First, in the same manner as preparation of the samples for calibration curve preparation, the cut flue-cured tobacco, the cut burley tobacco, the cut oriental tobacco, and the cut domestic tobacco, a filling capacity value of each of which was unknown, were used as they are as measurement samples. Then, with respect to each of 207 measurement samples obtained in this manner and made up of 93 samples of the flue-cured tobacco, 72 samples of the burley tobacco, 21 samples of the oriental tobacco, and 21 samples of the domestic tobacco, an absorption spectrum was measured at 0.5-nm intervals in a wavelength region of 800 nm to 2500 nm and an estimated filling capacity value was calculated by use of the estimated equation obtained above.

After a filling capacity of each of the measurement samples was estimated by the near infrared spectroscopy, the filling capacity of the each of the measurement samples was measured by the conventional filling capacity measuring method. Then, a correlation between the estimated filling capacity value obtained by the near infrared spectroscopy and the filling capacity value obtained by the conventional filling capacity measuring method was examined. The result is shown in FIG. 6 (see "Vali" in FIG. 6).

As shown in FIG. 6, also in a case where a sample for calibration curve preparation is in a form of cut rags, it is possible to obtain a calibration curve having a high coefficient of determination and, accordingly, estimate a filling capacity by the near infrared spectroscopy in the same manner as in a case where the measurement sample is in a form of powder. Further, it was demonstrated that also in the case where the measurement sample was in the form of cut rags, it was possible to accurately measure filling capacities of different varieties of leaf tobacco by using a common calibration curve.

INDUSTRIAL APPLICABILITY

The present invention can be applied to a designing and manufacturing of a cigarette.

The invention claimed is:

1. A method for measuring a filling capacity of a leaf tobacco, comprising the steps of:
   (i) providing leaf tobacco in a form of a powder;
   (ii) irradiating a near infrared ray on a sample of the leaf tobacco made only of leaf tobacco in the form of a powder, having a filling capacity by a near infrared spectroscopic measurement device;
   (iii) measuring a transmission absorption spectrum or a diffuse reflectance spectrum of the sample by the near infrared spectroscopic measurement device; and
   (iv) calculating an estimated filling capacity value by use of the transmission absorption spectrum or the diffuse reflectance spectrum thus measured and on the basis of a calibration curve which has been prepared in advance.

2. A method as set forth in claim 1, further comprising the step of:
   preparing the calibration curve by multivariate analysis by using the transmission absorption spectrum or the diffuse reflectance spectrum of each of a plurality of samples of the leaf tobacco, a filling capacity of which is known.

3. The method as set forth in claim 2, wherein:
   the multivariate analysis is multiple regression analysis or PLS regression analysis.

* * * * *